United States Patent [19]

Hanes et al.

[11] Patent Number: 5,004,568
[45] Date of Patent: Apr. 2, 1991

[54] CARBONYLATION OF ALLYLIC ETHERS TO ESTERS

[75] Inventors: Ronnie M. Hanes, Milford; Jack Kwiatek, Cincinnati, both of Ohio

[73] Assignee: National Distillers and Chemical Corporation, New York, N.Y.

[21] Appl. No.: 783,587

[22] Filed: Oct. 3, 1985

[51] Int. Cl.$^5$ ............................................. C09F 5/08
[52] U.S. Cl. ................................... 260/410; 560/207
[58] Field of Search ................. 260/410 C; 560/207

[56] References Cited

U.S. PATENT DOCUMENTS

| | | | |
|---|---|---|---|
| 2,876,254 | 3/1959 | Jenner et al. | 560/114 |
| 3,161,672 | 12/1964 | Zachry et al. | 560/207 |
| 3,367,961 | 2/1968 | Brewbaker | 560/207 |
| 3,427,344 | 2/1969 | Tsuji et al. | 560/114 |
| 3,530,168 | 9/1970 | Biale | 560/207 |
| 3,626,005 | 12/1971 | Scheben et al. | 560/114 |
| 3,652,255 | 3/1972 | Osieka et al. | 71/98 |
| 4,172,087 | 10/1979 | Knifton | 260/410.6 |
| 4,484,002 | 11/1984 | Lin | 562/519 |
| 4,519,956 | 5/1985 | Lin et al. | 562/519 |

OTHER PUBLICATIONS

Arzoumanidis et al., *J. Mol. Catal.*, 1980, 9(3), pp. 335–338.
Tsuji et al., *Journal of the American Chemical Society*, 86, pp. 4350–4353, (1964).
Arzoumanidis et al., *Chemical Abstract*, 95:61841h, (1981).

*Primary Examiner*—Charles F. Warren
*Attorney, Agent, or Firm*—Kenneth D. Tremain; Gerald A. Baracka

[57] ABSTRACT

A method is disclosed for the production of esters by reaction of an allylic ether with carbon monoxide in the presence of a catalytically effective amount of a Group VIII noble metal catalyst and a Group IB metal halide to obtain esters. The Group IB metal halide is present in an amount sufficient to prevent the catalyst from being converted into a Group VIII metal during the reaction. When the reaction is conducted in the presence of a quaternary ammonium salt the ester may be extracted by solvent extraction to minimize catalyst decomposition caused when extractive distillation is used to separate the ester.

25 Claims, No Drawings

CARBONYLATION OF ALLYLIC ETHERS TO ESTERS

TECHNICAL FIELD

The present invention generally relates to the production of esters by the reaction of allylic ethers with carbon monoxide in the presence of a metal compound as a catalyst.

PRIOR ART

Palladium chloride has been employed as a catalyst for the carbonylation of alkoxyoctadienes to alkyl nonadienoate esters; however, only low yields (less than 10%) of the ester were produced. Compounds of the palladium-type metals (i.e. the Group VIII noble metals) therefore did not appear to be good candidates for catalyzing reactions of this type even though some catalytic activity was noted with palladium chloride. The production of esters in this type of reaction on an industrial scale would require higher yields than the 10% initially observed.

Scheben, U.S. Pat. No. 3,626,005, discloses a process for the preparation of unsaturated acyl halides by carbonylating vinylic halides in the presence of a Group VIII noble metal catalyst such as palladium metal, the catalyst composition optionally containing metals such as gold, silver, copper and the like. Additionally, Jenner, et al., U.S. Pat. No. 2,876,254 also disclose a process for the preparation of esters from olefins, carbon monoxide and alcohols in the presence of a catalyst system comprising a Group VIII noble metal such as palladium and an alcohol-soluble salt of tin or germanium.

Various other U.S. Patents similarly teach the production of esters such as Knifton, U.S. Pat. No. 4,172,087 in which a process for the preparation of unsaturated aliphatic esters from aliphatic dienes such as butadiene is disclosed by reacting such unsaturated components with carbon monoxide and an alcohol in the presence of a palladium catalyst and an amine base. Group VIII metal catalysts are also disclosed for the preparation of esters in a similar manner by Zachry, et al., U.S. Pat. No. 3,161,672; Tsuji, et al., U.S. Pat. No. 3,427,344; Fenton, U.S. Pat. No. 3,652,655; Biale, U.S. Pat. No. 3,530,168 and Brewbaker, U.S. Pat. No. 3,367,961.

Tsuji, et al. J.A.C.S. 86, pp. 4350–4353 (1964) discloses the carbonylation of allyl ethyl ether in ethanol as a solvent to ethyl 2-butenoate in the presence of palladium chloride as a catalyst, whereas Chan, XXIII International Conference on Coordination Chemistry, July 29–Aug. 3, 1984, Univ. of Colorado (Abstract of Poster Presentation TH p 51-6) describes the affects of solvents, catalyst promoters and inhibitors on the palladium catalyst dicarbonylation of 1,4-difunctionalized-2-butenes.

None of the above references address the problems of overcoming the low yields and catalyst decomposition obtained when employing a palladium halide catalyst for the production of esters by the reaction of allylic ethers with carbon monoxide.

Additionally, in the manufacture of these esters using expensive Group VIII noble metal catalyst, it is necessary that the catalyst be recycled if it is to be employed on an industrial scale.

The ester product of the reaction may be separated from the reaction mixture by means of distillation, or vacuum distillation; however, both distillation processes require energy input which could also add to the cost of the process. Although solvent extraction processes are known in the art these known methods are not totally satisfactory for the separation of the ester from the catalyst either because of the cost of the solvents or the fact that some of the palladium catalyst is carried over into the ester that the catalyst is to be separated from.

SUMMARY OF THE INVENTION

Accordingly, it is an object of the present invention to overcome these and other difficulties encountered in the prior art.

It is a further object of the present invention to provide a catalyst for the reaction of an allylic ether with carbon monoxide for the production of an ester.

It is a further object of the invention to provide such a catalyst based on a Group VIII metal and especially a Group VIII metal halide.

It is an additional object of the present invention to provide a catalyst based on a Group VIII noble metal halide which is stable during the reaction of an allylic ether with carbon monoxide for the formation of an ester.

It is a further object of the present invention to provide a method for separating an ester from a catalyst comprising a Group VIII noble metal halide by means of a solvent extraction process.

These and other objects have been achieved according to the present invention which comprises a method for the production of esters comprising reacting an allylic ether with carbon monoxide in the presence of a catalytically effective amount of a catalyst and a Group IB metal halide and mixtures thereof to produce an ester, the catalyst comprising a Group VIII noble metal halide and mixtures thereof.

In another embodiment of the invention, the reaction is conducted by dissolving the catalyst in a solvent comprising a quaternary ammonium salt or phosphonium compound or a mixture of both that is liquid at the reaction temperature and the ester produced is separated from the catalyst by solvent extraction with a non-polar organic solvent.

DETAILED DESCRIPTION

In the production of esters by the reaction of an allylic ether with carbon monoxide in the presence of a Group VIII noble metal catalyst (i.e. ruthenium, rhodium, palladium, osmium, iridium and platinum and mixtures thereof) such as a palladium chloride catalyst it was observed that although the palladium chloride did in fact catalyze the reaction to the ester, the yields of the ester obtained were less than 10%. In trying to determine the cause for these low yields which are unacceptable for industrial scale reactions it was noted that during the course of the reaction the palladium chloride catalyst was unstable in that the catalyst was being converted into palladium metal. Although the prior art would indicate that palladium metal would catalyze the reaction of carbon monoxide with an allylic ether actual experience established that the formation of palladium metal during the carbonylation reaction detracted from the activity of the catalyst.

Means were sought to prevent the catalyst from being converted into the metal during the course of the reaction whereupon it was discovered that by employing a Group IB metal catalyst such as copper chloride (cupric or cuprous chloride) the instability of the Group VIII noble metal halides was overcome. Accordingly, the reaction is conducted in the presence of the Group VIII noble metal halide catalyst as described herein along with the Group IB metal halide which is present in an amount sufficient to prevent the catalyst from being converted into a Group VIII metal during the reaction.

The allylic ethers that may be reacted according to the method of the present invention comprise any acyclic or cyclic allylic ether having up to about 20 carbon atoms and especially those having from about 4 to about 20 carbon atoms. In addition, the aforesaid ethers may contain up to about 4 olefinically unsaturated positions and especially up to about 2 olefinically unsaturated positions along an acyclic hydrocarbon chain. The esters produced have up to about 21 carbon atoms and especially from about 5 to about 21 carbon atoms and similarly may be acyclic or may comprise an acyclic ester group attached to a cyclic group such as a cyclic hydrocarbon and have up to about 4 olefinically unsaturated positions along the acyclic hydrocarbon chain and especially up to about 2 of such olefinically unsaturated positions. The acyclic group of the ether or ester may be straight chain or a branched chain and has from 1 to about 6 and especially from 1 to about 4 carbon atoms.

Examples of various allylic ethers that may be reacted according to the method of the present invention comprises:

8-methoxy-1,6-octadiene
    methyl allyl ether
    methyl-2-butenyl ether
    3-methoxy-1-phenylpropene
    4-methoxy-1-phenyl-2-butene
    methyl 4-methoxy-crotonate
    1-methoxy-2-penten-4-one
    ethyl allyl ether
    isopropyl allyl ether
    8-isopropoxy-1,6-octadiene
    1-ethoxy-2-hexene
    3-ethoxy-1-phenylpropene
    1-methoxy-2-hexene
    1,4-dimethoxy-2-butene
    1-isopropoxy-2-pentene
    8-phenoxy-1,6-octadiene
    phenyl allyl ether
    benzyl allyl ether
    1-phenoxy-2-butene
    1-phenoxy-2-hexene
    1-phenoxy-2-penten-4-one
    1-phenoxy-2-pentene
    benzyl-2-butenyl ether The catalyst employed for the carbonylation reaction of the present invention comprises the Group VIII noble metal halides, i.e., the halides of ruthenium, rhodium, palladium, osmium, iridium, platinum and mixtures thereof, ruthenium, rhodium, palladium and platinum being preferred and palladium being especially preferred. The halides are selected from chloride, bromide and iodide and mixtures thereof, the chloride being preferred.

The Group IB metal halides that are employed in an amount sufficient to prevent the catalyst from being converted into a Group VIII metal during the reaction comprise copper, silver and gold, copper and silver being preferred and copper being especially preferred. Gold is not a Group IB metal of choice because of its cost and the difficulty in converting it into a halide such as by reacting gold metal with aqua regia. The less costly copper metal is preferred and may be used either as the cuprous halide or the cupric halide.

The catalyst is employed in the carbonylation reaction in an amount anywhere from about 0.005 mole % to about 1.0 mole % and especially from about 0.05 mole % to about 0.2 mole % based on the allylic ether employed in the reaction, this amount comprising a catalytically effective amount.

The amount of the Group IB metal halide employed in the reaction may be anywhere from about 5 to about 50 molar excess and especially from about 10 to about 25 molar excess based on the Group VIII metal, this amount comprising an amount sufficient to prevent said catalyst from being converted into said Group VIII metal during the carbonylation reaction. Any other amount of catalyst or Group IB metal halide may be employed and is readily determined by a person having ordinary skill in the art knowing that the catalyst as described herein will promote the carbonylation reaction noted above and that the Group IB metal halide will prevent the Group VIII metal of the catalyst from being formed during the carbonylation reaction.

The carbonylation reaction may be conducted at temperatures from about 50° C. to about 200° C. and at pressures from about 1,000 psig to about 5,000 psig. Other temperatures and pressures may also be employed and may be readily determined by a person having ordinary skill in the art having the within disclosure of the catalyzed carbonylation reaction.

In another aspect of the invention, it has been discovered that the esters produced according to the invention may be separated from the catalyst by solvent extraction when the carbonylation reaction is conducted in the presence of a solvent comprising quaternary ammonium or phosphonium compounds and mixtures thereof such as the quaternary ammonium salts and more particularly, the quaternary ammonium halides. Those quaternary ammonium salts that are liquid at the temperature of the carbonylation reaction are employed in this respect and generally comprise the tetra-alkyl ammonium halides especially the chlorides. Tetrabutyl ammonium chloride is especially suitable in this regard although other quaternary ammonium salts may be employed and include:

Tetrabutylammonium bromide
    Tetradecylammonium bromide
    Tetradodecylammonium bromide
    Benzyldimethyl(tetradecyl)ammonium chloride
    Benzyl(hexadecyl)dimethylammonium chloride
    Benzyldimethyl(dodecyl)ammonium bromide
    Benzyldimethyl(dodecyl)ammonium chloride
    Tetrahexylammonium chloride
    Benzyltributylammonium chloride
    Tetradecylammonium chloride Phosphonium compounds that may be employed comprise:

Tetrapentylphosphonium chloride
    Tetrahexylphosphonium chloride
    Tetrabutylphosphonium chloride
    Tetrabutylphosphonium bromide
    Tetrabutylphosphonium iodide
    Tetrahexylphosphonium bromide
    Benzyltributylphosphonium chloride When the carbonylation reaction is conducted in the presence of a quaternary ammonium salt or phosphonium compound, the ester obtained may be separated from the reaction mixture by means of solvent extraction whereby the ester is dissolved in a non-polar organic solvent such as a petroleum ether or the acyclic hydrocarbons and especially the aliphatic hydrocarbons having from about 4 to about 10 carbon atoms and especially those having from about 5 to about 8 carbon atoms. Either linear or branched chain acyclic hydrocarbon compounds may be employed in this respect although the linear ones are preferred. Examples of these hydrocarbons comprise pentane, hexane, heptane, octane, nonane and the like.

Other solvents that may be used comprise 2-methylpentane; 2-methylhexane; 3-methylhexane; 2-ethylpentane and 30–60 petroleum ether.

THE FOLLOWING EXAMPLES ARE ILLUSTRATIVE.

EXAMPLE 1

Methoxyoctadiene Carbonylation

To a 71 cc glass-lined Parr bomb was added 0.0052 g $PdCl_2$, 0.0511g $CuCl_2 \cdot 2H_2O$, 5 ml toluene and 5 ml 8-methoxy-1,6-octadiene. The bomb was purged 4 times, filled to 2,000 psig with CO and placed in a 100° C. shaker oven for 6 hours. No catalyst decomposition or polymer formation was observed.

GLC analysis of the reaction product was conducted on a Silar column and indicated 97% selectivity to methyl nonadienoate at about 48% conversion.

Thus, it can be seen that the catalyst of the present invention when employed in the carbonylation of 8-methoxy-1,6-octadiene provided excellent selectivities and yields of methyl-3,8-nonadienoate.

EXAMPLE 2

To a 71 cc glass-lined Parr bomb was added 0.0055 g $PdCl_2$, 0.0118g $CuCl_2 \cdot 2H_2O$ and 5 ml 8-methoxy-1,6-octadiene. The bomb was purged 4 times, filled to 2,000 psig with CO and placed in a 100° C. shaker oven for 6 hours. A trace of a black precipitate was observed as a decomposition product. The product was analyzed as in Example 1 and 93% selectivity to methyl-3,8-nonadienoate at 8% conversion was obtained.

EXAMPLE 3

To a 71 cc glass-lined Parr bomb was added 0.0058 g $PdCl_2$, 0.0752 g $CuCl_2 \cdot 2H_2O$, 5 ml 8-methoxy-1,6-octadiene and 2 g tetrabutylammonium chloride. The bomb was purged 4 times, filled to 2,000 psig with CO and placed in a 100° C. shaker oven for 6 hours. No catalyst decomposition was observed. A GLC analysis was conducted on the product solution as in Example 1 and after the analysis, 5 ml 8-methoxy-1,6-octadiene was added to the product solution. The product solution with the 8-methoxy-1,6-octadiene was again added to a 71 cc glass-lined Parr bomb, the bomb purged 4 times and filled to 2,000 psig with CO and placed in a 100° C shaker oven for 6 hours. After the second reaction, a large amount of black precipitate was observed.

The GLC analyses of both the first and second runs indicate 92% selectivity to methyl-3,8-nonadienoate at conversions of 60% for the first run and 38% for the second run.

The foregoing example illustrates that when 0.033 mmoles $PdCl_2$ are employed in combination with 0.44 mmoles $CuCl_2$, catalyst decomposition is not minimized in the second run.

EXAMPLE 4

To a 71 cc glass-lined Parr bomb was added 0.0048 g $PdCl_2$, 0.0405 g anhydrous $CuCl_2$, 5 ml toluene and 5 ml 8-methoxy-1,6-octadiene. The bomb was purged 4 times and filled to 2,000 psig with CO and placed in 100° C shaker oven for 6 hours. A small amount of dark precipitate was observed following the reaction. The reaction product again was analyzed by the same method employed in example 1 and methyl-3,8-nonadienoate was obtained at 96% selectivity and 87% conversion of 8-methoxy-1,6-octadiene.

EXAMPLE 5

To a 71 cc glass-lined Parr bomb was added 0.0063 g $PdCl_2$, 0.0772 g $CuCl_2 \cdot 2H_2O$, 1.97 g tetrabutylammonium chloride and 5 ml 8-methoxy-1,6-octadiene. The bomb was purged 4 times, filled to 2,000 psig with CO and placed in a 100° C. shaker oven for 6 hours. A large amount of black precipitate was observed. The product solution was extracted with two 7 ml portions of petroleum ether and analyzed in the same manner as set forth in example 1. 92% selectivity to methyl-3,8-nonadienoate was observed at 70% conversion of 8-methoxy-1,6-octadiene. The catalyst residue was returned to the bomb with 5 ml 8-methoxy-1,6-octadiene and 0.0935 g $CuCl_2.2H_2O$ after which the bomb was purged 4 times and filled to 2,000 psig with CO and placed in a 100° C. shaker oven for 6 hours.

The product was analyzed in the same manner as set forth in Example 1 and 89% selectivity to methyl-3,8-nonadienoate was observed at 80% conversion 8-methoxy-1,6-octadiene.

A trace of black precipitate was observed in the bottom of the bomb along with a residue. The residue was extracted three times with 10 ml petroleum ether and to the residue, extracted with the petroleum ether, was added 5 ml 8-methoxy-1,6-octadiene which again was charged to a 71 cc glass-lined Parr bomb. The bomb was purged 4 times, filled to 2,000 psig with CO and placed in a 100° C. shaker oven for 6 hours. A large amount of black precipitate was observed.

The product was analyzed in the same manner as set forth in Example 1 and 86% selectivity to methyl-3,8-nonadienoate was observed at 72% conversion of 8-methoxy-1,6-octadiene.

The foregoing data illustrate the carbonylation of 8-methoxy-1,6-octadiene to methyl-3,8-nonadienoate with palladium chloride as a catalyst. The palladium chloride is reduced during the reaction and falls out of solution; however, by the addition of cupric chloride to the reaction solution in molar excess over the palladium, the catalyst was stabilized so that high 8-methoxy-1,6-octadiene conversions may be realized.

The use of a quaternary ammonium salt as a solvent with the catalyst system allows removal of product ester (methyl-3,8-nonadienoate) by extraction with a non-polar organic solvent such as petroleum ether, pentane, hexane and the like. The soluble palladium catalyst, as illustrated in the previous examples may then be recycled without being exposed to a distillation step.

The esters obtained according to the method of the invention may be hydrogenated and used as lubricants, plasticizers or functional fluids or may be hydrolyzed to form acids having unsaturated groups. The acids obtained may be incorporated into polyesters manufactured from phthalic anhydride, glycols and maleic anhydride and which are subsequently cross-linked with styrene. The unsaturated acid obtained provides a site for cross-linking with styrene or equivalent monomers.

Although the invention has been described by reference to some embodiments, it is not intended that the novel method for the production of esters by carbonylation of an allylic ether in the presence of a catalyst be limited thereby but that modifications thereof are intended to be included as falling within the broad scope and spirit of the foregoing disclosure and the following claims.

What is claimed is:

1. A method for the production of esters comprising reacting an allylic ether with carbon monoxide to obtain an ester, said reaction conducted in the presence of a catalytically effective amount of a halide of a Group VIII noble metal and a Group IB metal halide, said Group IB metal halide present in an amount sufficient to prevent said halide of a Group VIII noble metal from being converted into said Group VIII noble metal during said reaction.

2. The method of claim 1 where said allylic ether has from about 4 to about 20 carbon atoms and said ester has from 5 to about 21 carbon atoms.

3. The method of claim 1 wherein said allylic ether comprises an alkoxyalkadiene and said ester comprises an alkyl alkadienoate.

4. The method of claim 1 where said halides of said Group VIII metal and said Group IB metal are selected from chloride, bromide or iodide and mixtures thereof.

5. The method of claim 4 where said Group VIII metal comprises a member selected from ruthenium, rhodium, palladium and platinum and mixtures thereof.

6. The method of claim 5 where said Group VIII metal comprises palladium and said Group IB metal comprises copper.

7. The method of claim 5 where said allylic ether comprises a lower alkoxyalkadiene having from 4 carbon atoms to about 20 carbon atoms and said ester comprises a lower alkyl alkadienoate.

8. The method of claim 4 where said reaction is conducted at temperatures from about 50° C. to about 200° C. and at pressures from about 1,000 psig to about 5,000 psig.

9. The method of claim 7 wherein said reaction is conducted at temperatures from about 50° C. to about 200° C. and at pressures of from about 1,000 psig to about 5000 psig.

10. A method for the production of esters comprising reacting methoxyoctadiene with carbon monoxide to obtain methyl nonadienoate, said reaction conducted in the presence of a catalytically effective amount of a halide a Group VIII noble metal and a Group IB metal halide, said Group IB metal halide present in an amount sufficient to prevent said halide of a Group VIII noble metal from being converted into said Group VIII noble metal during said reaction.

11. The method of claim 10 where said methoxyoctadiene comprises 8-methoxy-1,6-octadiene and said methyl nonadienoate comprises methyl-3,8-nonadienoate.

12. The method of claim 10 where said halide of said Group VIII metal and said Group IB metal is selected from chloride, bromide or iodide and mixtures thereof.

13. The method of claim 12 where said Group VIII metal comprises a member selected from ruthenium, rhodium, palladium and platinum.

14. The method of claim 13 where said Group VIII metal comprises palladium and said Group IB metal comprises copper.

15. The method of claim 14 where said reaction is conducted at temperatures of from about 50° to about 200° C. at pressures from about 1,000 psig to about 5,000 psig.

16. A method for the production of esters comprising reacting an allylic ether with carbon monoxide to obtain an ether, said reaction conducted in the presence of a catalytically effective amount of a catalyst comprising a halide of a Group VIII noble metal and a Group IB metal halide in an amount sufficient to prevent said halide of said Group VIII metal from being converted into said Group VIII metal during said reaction, said catalyst dissolved in a reaction solvent, liquid at the temperature of said reaction, selected from the group consisting of a quaternary ammonium salt, a phosphonium compound and mixtures thereof wherein said ester product is separated from said catalyst by solvent extraction of said ester with a non-polar organic solvent.

17. The method of claim 16 where said reaction solvent is a tetraalkyl ammonium halide.

18. The method of claim 16 where said reaction solvent is tetrabutyl ammonium chloride and said extractive solvent is selected from the group consisting of petroleum ether and acyclic hydrocarbons.

19. A method for the production of esters comprising reacting methoxyoctadiene with carbon monoxide to obtain methyl nonadienoate, said reaction conducted in the presence of a catalytically effective amount of a catalyst comprising a halide of a Group VIII noble metal and a Group IB metal halide in an amount sufficient to prevent said halide of said Group VIII metal halide from being converted into said Group VIII metal during said reaction, said catalyst dissolved in a solvent, liquid at the temperature of said reaction, selected from the group consisting of a quarternary ammonium salt, a phosphonium compound and mixtures thereof wherein said methyl nonadienoate is separated from said catalyst by solvent extraction of said methyl nonadienoate with a non-polar organic solvent.

20. The method of claim 19 where said reaction solvent is a tetraalkyl ammonium halide.

21. The method of claim 19 wherein said reaction solvent is tetrabutyl ammonium chloride and said extraction solvent is selected from the group consisting of petroleum ether and acyclic hydrocarbons.

22. A method for the production of esters consisting essentially of reacting an allylic ether with carbon monoxide in the presence of a catalytically effective amount of a halide of a Group VIII noble metal and a Group IB metal halide, said Group IB metal halide present in an amount sufficient to prevent said halide of a Group VIII noble metal from being converted into said Group VIII noble metal during said reaction whereby an ester is obtained.

23. The method of claim 22 wherein said allylic ether is an alkoxyalkadiene containing from about 4 to about 20 carbon atoms and said ester is an alkyl alkadienoate containing from about 5 to about 21 carbon atoms.

24. The method of claim 23 wherein said Group VIII noble metal is palladium and said Group IB metal is copper.

25. The method of claim 24 wherein said alkoxyalkadiene is 8-methoxy-1,6-octadiene and said alkyl alkadienoate is methyl-3,8-nonadienoate.

* * * * *